(12) United States Patent
Carroccio et al.

(10) Patent No.: US 11,628,277 B1
(45) Date of Patent: Apr. 18, 2023

(54) DEVICES, SYSTEMS, AND METHODS FOR HOLDING MEDICAL DEVICES

(71) Applicant: American Endoscopic Innovations, LLC, Charlton, MA (US)

(72) Inventors: Alfio Carroccio, Manhasset, NY (US); James Barry, Charlton, MA (US)

(73) Assignee: American Endoscopic Innovations, LLC, Charlton, MA (US)

( * ) Notice: Subject to any disclaimer, the term of this patent is extended or adjusted under 35 U.S.C. 154(b) by 0 days.

(21) Appl. No.: 17/681,023

(22) Filed: Feb. 25, 2022

(51) Int. Cl.
| A61M 25/02 | (2006.01) |
| A61M 25/01 | (2006.01) |
| A61B 17/28 | (2006.01) |
| A61M 5/14 | (2006.01) |
| A61M 25/09 | (2006.01) |

(52) U.S. Cl.
CPC ............ *A61M 25/02* (2013.01); *A61M 25/01* (2013.01); *A61M 25/09* (2013.01); *A61B 17/282* (2013.01); *A61B 2017/2808* (2013.01); *A61B 2017/2825* (2013.01); *A61M 5/1418* (2013.01); *A61M 2025/024* (2013.01); *A61M 2025/0293* (2013.01); *A61M 2025/09116* (2013.01); *A61M 2025/09125* (2013.01)

(58) Field of Classification Search
CPC ............ A61M 25/02; A61M 2025/024; A61M 25/01; A61M 25/09; A61M 2025/09125; A61M 2025/0293; A61M 5/1418; A61M 5/344; A61M 2025/0177; A61M 2039/0673; A61M 39/28; A61M 39/284; A61M 2005/244; A61M 25/09041; A61B 2017/2825
See application file for complete search history.

(56) References Cited

U.S. PATENT DOCUMENTS

| 9,101,738 B2 | 8/2015 | Eden |
| 10,285,768 B2 | 5/2019 | O'Brien |
| 10,569,059 B2 | 2/2020 | Bierman |
| 2006/0094987 A1* | 5/2006 | van Erp .......... A61M 25/09041 |
| | | 600/585 |

(Continued)

FOREIGN PATENT DOCUMENTS

| DE | 10 2010 011 222 B4 | 4/2015 |
| JP | 11-151299 | 6/1999 |

(Continued)

*Primary Examiner* — Katherine H Schwiker
*Assistant Examiner* — Robert F Allen
(74) *Attorney, Agent, or Firm* — Fish & Richardson P.C.

(57) ABSTRACT

A medical clip for holding a medical device. The medical clip includes a first jaw and a second jaw rotatably coupled to the first jaw, the first jaw and the second jaw being rotatable with respect to each other between a closed position and an open position;

an elastomeric insert configured to be positioned between the first jaw and the second jaw. The elastomeric insert defining a cavity having a cavity depth that receives a medical device between the first jaw and the second jaw. In the closed position, a distal face of the first jaw and the second jaw define a distal opening configured to receive a portion of the medical device through the distal opening; and, a proximal face of the first jaw and the second jaw define a proximal opening configured to receive a second portion of the medical device through the proximal opening.

19 Claims, 10 Drawing Sheets

(56) References Cited

U.S. PATENT DOCUMENTS

| | | |
|---|---|---|
| 2006/0195117 A1 | 8/2006 | Rucker et al. |
| 2007/0161969 A1 | 7/2007 | Andersen |
| 2008/0092349 A1* | 4/2008 | Cofer .................. A61M 5/1418 24/487 |
| 2014/0324024 A1* | 10/2014 | Tejani ................... A61M 25/02 604/178 |
| 2015/0119845 A1 | 4/2015 | Collins et al. |
| 2015/0141960 A1 | 5/2015 | Mauch |
| 2015/0141962 A1 | 5/2015 | Collins et al. |
| 2018/0021507 A1* | 1/2018 | Tamrazi ................ A61M 25/09 24/16 R |
| 2019/0307990 A1 | 10/2019 | Fogg et al. |
| 2020/0246595 A1 | 8/2020 | Bierman |
| 2020/0289744 A1 | 9/2020 | Tamrazi et al. |
| 2021/0268255 A1* | 9/2021 | O'Neil ............... A61M 39/1011 |

FOREIGN PATENT DOCUMENTS

| | | |
|---|---|---|
| JP | 2010-500907 A | 1/2010 |
| JP | 2018-505753 A | 3/2018 |
| JP | 2021-516092 A | 7/2021 |

\* cited by examiner

DEVICES, SYSTEMS, AND METHODS FOR HOLDING MEDICAL DEVICES

This document describes devices, systems, and methods related to positional securing of medical devices. Specifically, a device that can assist in treating patients while utilizing a catheter or endoscopic-based therapies. For example, devices that can secure a catheter or guidewire, to an introducer sheath to eliminate movement of the catheter or guidewire, which can prevent the loss of access to a targeted location in the patient's body. Additional implementations provide a device that secures an endoscopic instrument to the working channel port of an endoscope thus fixing the position of the instrument to the endoscope.

BACKGROUND

In general, minimally invasive medical procedures can utilize catheters, endoscopes, and other medical instruments to perform therapies and imaging to patients. Minimally invasive medical procedures can be complex and involve several medical instruments in use concurrently and/or at various times during a procedure. The positional relationship between medical instruments is important for patient safety, successful procedures, consistency of treatment, and ease of use for medical professionals.

Previous approaches to ensure a fixed positioning of a catheter, guidewire, or instrument while performing other steps in minimally invasive surgical procedures include using an assistant to hold the instruments such as a catheter, guidewire, or endoscope or other instrument. The use of a medical assistant requires additional personnel, can cause crowding in the operative area, and can cause communication errors. The additional personnel adds cost to the procedure, and the personnel may move, thus causing differential movement of the medical instruments. Other solutions include utilizing a surgical clamp or adhesive tape to secure the medical instruments to sterile drapes or equipment in the vicinity of an introducer sheath or endoscope. Utilizing a surgical clamp or adhesive tape can cause damage to the medical instrument by a nonspecific or inappropriate clamping device. These clamping devices may not be fixed to the medical instrument which allows undesirable differential movement of a catheter, guidewire, or other medical instrument. Hemostatic clamps can be heavy and can pull and/or weigh down instruments or surgical drapes. Additionally, repositioning of the catheter, guidewire, or instrument can be difficult, and can include multiple operations or additional personnel.

SUMMARY

The document generally relates to devices for holding and/or securing medical instruments together during medical procedures. More specifically, the document relates to medical clips with inserts that are configured to receive medical devices.

Particular implementations described herein include a medical clip for holding a medical device. The medical clip also includes a first jaw. The clip also includes a second jaw, the second jaw being rotatably coupled to the first jaw, the first jaw and the second jaw being rotatable with respect to each other between a closed position and an open position. The clip also includes an elastomeric insert configured to be positioned between the first jaw and the second jaw, the elastomeric insert defining a proximal cavity having a cavity depth that is dimensioned to receive a medical device between the first jaw and the second jaw. The clip also includes a first lever connected to the first jaw. The clip also includes a second lever connected to the second jaw, the first lever and the second lever being configured to control each of the first jaw and the second jaw between the closed position and the open position. The clip also includes where, based on the medical clip being in the closed position, a distal face of the first jaw and the second jaw define a distal opening configured to receive a portion of the medical device through the distal opening. The clip also includes where, based on the medical clip being in the closed position, a proximal face of the first jaw and the second jaw define a proximal opening configured to receive a second portion of the medical device through the proximal opening.

In some implementations, the medical clip can optionally include one or more of the following features. The medical clip can include a lateral face that extends between the distal face and the proximal face of each of the first jaw and the second jaw, the lateral face of the first jaw defining a first part of a lateral opening and the lateral face of the second jaw defining a second part of the lateral opening, where the lateral opening is configured to accommodate a lateral port of the medical device. The elastomeric insert defines a proximal recess that aligns with the proximal opening of the first jaw and the second jaw. The elastomeric insert has a first insert connected to the first jaw and a second insert connected to the second jaw, the first insert and second insert being symmetrical. The elastomeric insert has a durometer from 20 A to 80 A. The elastomeric insert may include collapsible ribs that extend circumferentially around the proximal cavity, the collapsible ribs being configured to collapse when the medical device is inserted within the proximal cavity. A distal portion of the elastomeric insert defines an auxiliary channel that extends distally through the distal portion to a distal face of the elastomeric insert. A distal portion of the elastomeric insert is flat and extends distally through the distal portion to a distal face of the elastomeric insert. The first jaw and the second jaw are symmetrical. The medical clip may include: a hinge connected to each of the first jaw and the second jaw, the first jaw and the second jaw being rotatable about the hinge. The medical clip may include; a torsion spring disposed about the hinge providing force to close the first and second jaws automatically when the first and second levers are released. The elastomeric insert further may include a distal portion that has a distal depth that is less than the cavity depth. Each of the first jaw and the second jaw has a curved shape that extends between the proximal face and the distal face.

Particular implementations described herein include a clip for securing a medical device. The clip also includes a first jaw having a curved shape that extends between a proximal face of the clip to a distal face of the clip. The clip also includes a second jaw having a curved shape that extends between the proximal face of the clip and the distal face of the clip, the first jaw and the second jaw being rotatable with respect to each other between a closed position and an open position. The clip also includes an elastomeric insert having a first insert configured to be received within the first jaw and a second insert configured to be received within the second jaw, the elastomeric insert defining a proximal cavity having a cavity depth that is dimensioned to receive a medical device between the first jaw and the second jaw. The clip also includes a first lever connected to the first jaw. The clip also includes a second lever connected to the second jaw, the first lever and the second lever being configured to control each of the first jaw and the second jaw between the closed position and the open position. The clip also includes where, based on the clip being in the closed position, a distal face of the first jaw and the second jaw define a distal opening configured to receive a portion of the medical device through the distal opening. The clip also includes where, based on the clip being in the closed position, a proximal face of the first jaw and the second jaw define a proximal opening configured to receive a second portion of the medical device through the proximal opening.

In some implementations, the clip can optionally include one or more of the following features. The clip can include the elastomeric insert that defines a proximal recess that aligns with the proximal opening of the first jaw and the second jaw. The elastomeric insert has a first insert connected to the first jaw and a second insert connected to the second jaw, the first insert and second insert being symmetrical. The elastomeric insert has a durometer from 20 A to 80 A. A distal portion of the elastomeric insert is flat and extends distally through the distal portion to a distal face of the elastomeric insert. The first jaw and the second jaw are symmetrical.

Particular implementations described herein include a method of holding a medical device using a clip. The method of holding also includes providing a clip for holding a medical device, the clip may include: a first jaw, a second jaw, the second jaw being rotatably coupled to the first jaw and a second jaw, the first jaw and the second jaw being rotatable with respect to each other about a hinge between a closed position and an open position, an elastomeric insert positioned between an internal surface of the first jaw and an internal surface of the second jaw, the elastomeric insert having a proximal cavity with a cavity depth that is dimensioned to receive a medical device between the first jaw and the second jaw, a first lever connected to the first jaw, and a second lever connected to the second jaw, the first lever and the second lever being configured to control each of the first jaw and the second jaw between the closed position and the open position. The holding also includes opening the first and second jaws to place the clip in the open position. The holding also includes inserting a portion of the medical device in the proximal cavity of the elastomeric insert. The holding also includes closing the first and second jaws to place the clip in the closed position such that the medical device is held by the elastomeric insert.

The devices, system, and techniques described herein may provide one or more of the following advantages. For example, the medical clip can remove the need for an assistant to maintain position of a catheter, guidewire or endoscopic instrument during a procedure. Second, the medical clip can facilitate the single handed use of the medical clip to secure catheter, guidewire, or instrument. Third, the medical clip can improve safety by removing securement of a catheter, guidewire, or instrument with an inappropriate device or adhesive to nearby sterile drapes or other equipment. Another advantage is the medical clip can improve safety by maintaining the catheter, guidewire or instrument integrity and by avoiding damage that can occur with current securing methods (e.g., securing to drapes or other equipment). The medical clip is advantageous by maintaining catheter, guidewire, or instrument position within the targeted anatomy. Another advantage is the medical clip allows for multiple sizes and types of catheters, guidewires, or instruments to be fixed with a single clip. Additionally, the medical clip improves safety and cleanliness of surgical materials by providing a sterilized medical clip that can be disposed of after one use.

The details of one or more implementations are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

This document generally relates to devices, systems, and methods related to positional securing of medical devices. Specifically, a device that can assist in treating patients while utilizing a catheter or endoscopic-based therapies. For example, devices that can secure a catheter or guidewire, to an introducer sheath to eliminate movement of the catheter or guidewire, which can prevent the loss of access to a targeted location in the patient's body. Additional implementations provide a device that secures an endoscopic instrument to the working channel port of an endoscope thus fixing the position of the instrument to the endoscope.

Figure 1:
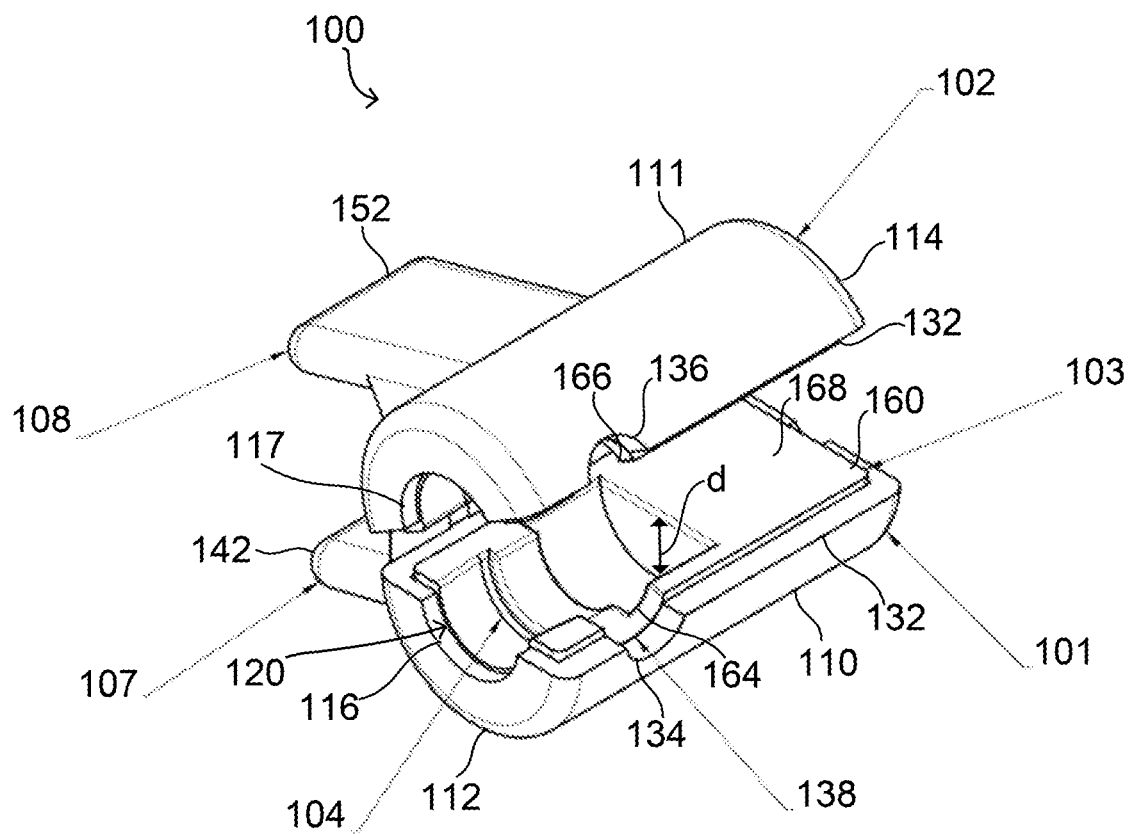
FIG. 1 shows a top, front perspective view of an example medical clip in an open position.
Figure 2:
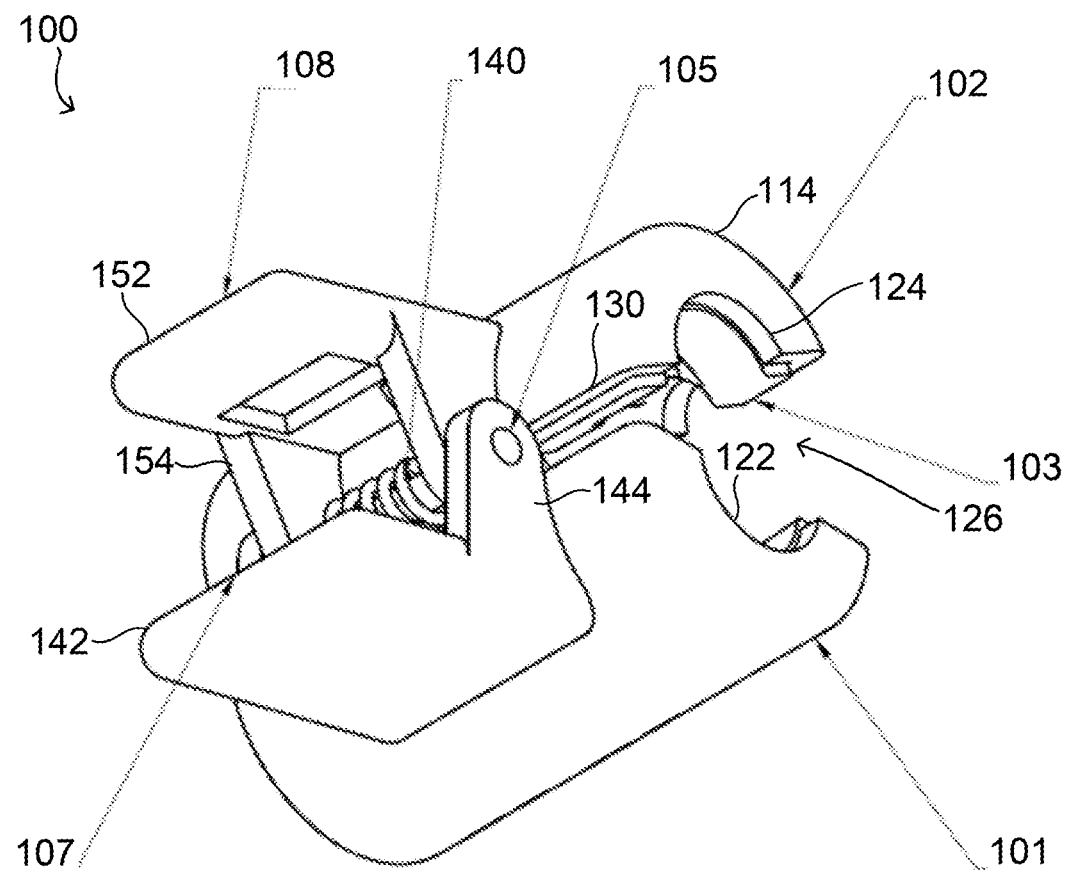
FIG. 2 shows a bottom, rear perspective view of the medical clip of FIG. 1 in an open position.

Referring to the figures, FIGS. 1 and 2 illustrate an example medical clip 100 as described herein. The medical clip 100 is depicted in an open position in FIGS. 1 and 2 to show components contained therein. The medical clip 100 can include a first jaw 101 and a second jaw 102, the first jaw 101 and the second jaw 102 have a hollow section to accept various inserts 103 that are internally shaped with a cavity 104 to mate with medical instruments such as medical introduction sheaths and working channel ports on endoscopes. The first jaw 101 and the second jaw 102 are attached together at a hinge 105. A torsion spring 140 can be wound around the hinge 105 to provide resistance to opening and automatic closure of the first jaw 101 and second jaw 102. The hinge 105 is connected to a first lever 107 and a second lever 108 that can provide a gripping and/or pinching area where a user can apply an opening force to the medical clip 100 to open the first jaw 101 and second jaw 102.

In some aspects, the first jaw 101 and second jaw 102 are symmetrical. For example, each of the first jaw 101 and the second jaw 102 has a curved exterior shell 110, 111 that extends between a proximal face 112 of each of the first jaw 101 and the second jaw 102 and a distal face 114 of each of the first jaw 101 and the second jaw 102. The curved exterior shell 110, 111 of each of the first jaw 101 and second jaw 102 also extends between a medial face 130 and a lateral face 132.

The proximal face 112 includes a curved inner surface 116 on the first jaw 101 and a curved inner surface 117 on the second jaw 102, the curved inner surfaces 116, 117 can include a similar curved profile to the curved exterior shells 110, 111. In some aspects, the curved inner surfaces 116, 117 match the curvature of the curved exterior shells 110, 111. In some aspects, the curved inner surface 116 in the proximal face 112 of the first jaw 101 aligns with the curved inner surface 117 in the second jaw 102 when the medical clip 100 is in the closed position shown in FIG. 3. The alignment of the curved inner surfaces 116, 117 at the proximal face 112 defines a proximal opening 120 that is configured to receive a portion of a medical device through the proximal opening 120, as described in further detail below.

As illustrated in FIG. 2, the distal face 114 includes a curved inner surface 122 on the first jaw 101 and a curved surface 124 on the second jaw 102, the curved inner surfaces 122, 124 can include a similar curved profile to the curved exterior shells 110, 111. In some aspects, the curved inner surfaces 122, 124 match the curvature of the curved exterior shells 110, 111. In some aspects, the curved inner surface 122 in the distal face 114 of the first jaw 101 aligns with the curved inner surface 124 in the second jaw 102 when the medical clip 100 is in the closed position shown in FIG. 3. The alignment of the curved inner surfaces 122, 124 at the distal face 114 defines a distal opening 126 that is configured to receive a portion of a medical device through the distal opening 126, as described in further detail below. In some aspects, the distal opening 126 can be the same size and shape as the proximal opening 120. In other aspects, the distal opening 126 and the proximal opening 120 can be different sizes and/or different shapes.

Figure 3:
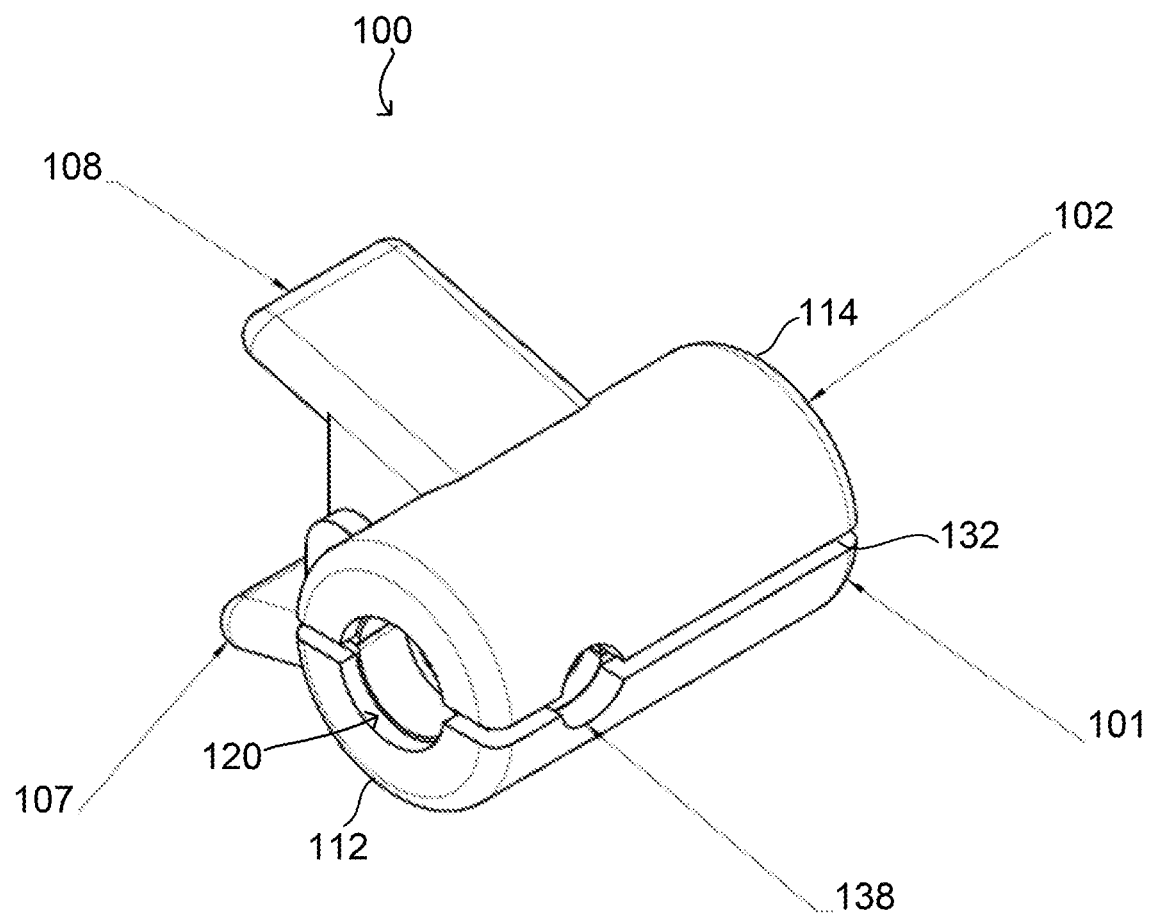
FIG. 3 shows a top, front perspective view of the medical clip of FIG. 1 in a closed position.

As illustrated in FIGS. 1-3, the curved exterior shell 110, 111 of each of the first jaw 101 and second jaw 102 extends between the medial face 130 and the lateral face 132. The medial face 130 of each of the first jaw 101 and the second jaw 102 extends between the proximal face 112 and distal face 114, and extends across and between each of the first lever 107 and the second lever 108, respectively. The medial face 130 of each of the first jaw 101 and second jaw 102 are configured to align with each other when the medical clip 100 is in the closed position shown in FIG. 3.

The lateral face 132 extends between the proximal face 112 and distal face 114 of each of the first jaw 101 and the second jaw 102. The lateral face 132 includes a curved lateral surface 134 on the first jaw 101 and a curved lateral surface 136 on the second jaw 102, the curved lateral surfaces 134, 136 can share a curved profile where the curved lateral surfaces 134, 136 extend into each of the first jaw 101 and second jaw 102 at equal curved shapes. In some aspects, the curved lateral surfaces 134, 136 can have different curved shapes and/or sizes.

In some aspects, the curved lateral surface 134 in the lateral face 132 of the first jaw 101 aligns with the curved lateral surface 136 in the second jaw 102 when the medical clip 100 is in the closed position shown in FIG. 3. The alignment of the curved lateral surfaces 134, 136 at the lateral face 132 defines a lateral opening 138 that is configured to receive a portion of a medical device through the lateral opening 138, as described in further detail below. In some aspects, the curved lateral surface 134 in the lateral face 132 of the first jaw 101 defines a first part of the lateral opening 138, and the curved lateral surface 136 in the lateral face 132 of the second jaw 102 defines a second part of the lateral opening 138.

As shown in FIGS. 1-3, the lateral curved surfaces 134, 136 can be positioned closer to the proximal face 112 than the distal face 114 along the lateral face 132 of the first jaw 101 and the second jaw 102. In some aspects, the curved lateral surfaces 134, 136 can be centered between the proximal face 112 and the distal face 114 along the lateral face 132. In some aspects, the curved lateral surfaces 134, 136 can be positioned closer to the distal face 114 than the proximal face 112 along the lateral face 132.

FIG. 2 shows the hinge 105 connected to each of the first jaw 101 and the second jaw 102. In some aspects, the hinge 105 is connected to the first jaw 101 via the first lever 107, and the hinge 105 is connected to the second jaw 102 via the second lever 108. The first jaw 101 and the second jaw 102 are rotatably coupled to each other at the hinge 105. In some aspects, the term "rotatably coupled" can refer to the connection mechanism (e.g., hinge 105) between the first jaw 101 and second jaw 102 that allows the first jaw 101 and second jaw 102 to rotate with respect to each other. In some aspects, the hinge 105 includes a pin that extends between the first lever 107 and the second lever 108. The first jaw 101 and the second jaw 102 are rotatable with respect to each other about the hinge 105 between a closed position (e.g., FIG. 3) and an open position (e.g., FIG. 1).

In some aspects, the torsion spring 140 is disposed about the hinge 105. The torsion spring 140 provides a force to close the first jaw 101 and the second jaw 102 automatically when the first lever 107 and the second lever 108 are released. The torsion spring 140 biases the first jaw 101 and second jaw 102 in the closed position shown in FIG. 3. Actuation of the first lever 107 and second lever 108 towards each other with a force that overcomes the force of the torsion spring 140 allows the first jaw 101 and the second jaw 102 to open into the open position shown in FIGS. 1 and 2. In some aspects, the torsion spring 140 can include elastic elements other than a spring to bias the first jaw 101 and the second jaw 102 in the closed position. Non-limiting examples of elastic elements that could be implemented include: one or more tension bars, one or more tensioning belts, one or more clamps, and other elastic elements that can bias the first jaw 101 and the second jaw 102 in the closed position.

The first lever 107 is connected to the first jaw 101 and is positioned along the medial face 130 of the first jaw 101. The first lever 107 includes an arm portion 142 that extends outwardly from the medial face 130 of the first jaw 101. The arm portion 142 of the first jaw 101 provides a surface area for a user to grip the first jaw 101. The arm portion 142 is connected to a base portion 144 of the first jaw 101. The base portion 144 extends vertically from the arm portion 142 on each of the proximal side and the distal side to openings that are configured to receive the hinge 105. The arm portion 142 and the base portion 144 are dimensioned to match the contouring of curved exterior shell 110. The base portion 144 has a width that is configured to receive a base portion 154 of the second lever 108 within the base portion 144.

The second lever 108 is connected to the second jaw 102 and is positioned along the medial face 130 of the second jaw 102. The second lever 108 includes an arm portion 152 that extends outwardly from the medial face 130 of the second jaw 102. The arm portion 152 of the second lever 108 provides a surface area for a user to grip the second lever 108. The arm portion 152 is connected to the base portion 154 of the second lever 108. The base portion 154 extends vertically from the arm portion 152 on each of the proximal side and the distal side to openings that are configured to receive the hinge 105. The arm portion 152 and the base portion 154 are dimensioned to match the contouring of curved exterior shell 111. The base portion 154 has a width that is configured to fit within the width of the base portion 144 of the first lever 107.

The first lever 107 and the second lever 108 can be actuated toward each other by a user that can grip the first arm portion 142 and the second arm portion 152 which causes the lateral face 132 of each of the first jaw 101 and second jaw 102 to rotate away from each other, placing the medical clip 100 in the open position. The medical clip 100 is in the open position shown in FIGS. 1 and 2, which exposes the elastomeric insert 103 of the medical clip 100.

Referring to FIGS. 1 and 2, the elastomeric insert 103 is dimensioned to be positioned between the first jaw 101 and the second jaw 102. The elastomeric insert 103 can include a first insert 160 that is positioned in the first jaw 101 and a second insert 162 that is positioned in the second jaw 102. In some aspects, the first insert 160 and the second insert 162 can be symmetrical. In some aspects, the first insert 160 is dimensioned to fill an internal profile of the first jaw 101 and the second insert 162 is dimensioned to fill an internal profile of the second jaw 102.

The elastomeric insert 103 defines the cavity 104 that can be in a proximal portion of the first insert 160 and the second insert 162, the proximal portion is closer to the proximal face 112 than the distal face 114. The cavity 104 has a cavity depth "d" in each of the first insert 160 and the second insert 162 that is dimensioned to receive a medical device between the first jaw 101 and the second jaw 102. The cavity depth d can be dimensioned and shaped to align the cavity 104 with each of the curved inner surfaces 116, 117 at the proximal face 112 of the first jaw 101 and the second jaw 102. The alignment of the cavity depth d and the curved inner surfaces 116, 117 provides access to the cavity 104 via the proximal opening 120 that is configured to receive a portion of a medical device through the proximal opening 120.

In some aspects, the elastomeric insert 103 includes a curved insert surface 164 on the first insert 160 and a curved insert surface 166 on the second insert 162, the curved insert surfaces 164, 166 can share a curved profile where the curved insert surfaces 164, 166 extend into each of the first insert 160 and second insert 162 along a lateral side at equal curved shapes. In some aspects, the curved insert surfaces 164, 166 can have different curved shapes and/or sizes.

In some aspects, the curved insert surface 164 in the first insert 160 aligns with the curved insert surface 166 in the second insert 162 when the medical clip 100 is in the closed position shown in FIG. 3. The alignment of the curved insert surfaces 164, 166 also aligns with the curved lateral surfaces 134, 136 at the lateral face 132 to provide access to the cavity 104 via the lateral opening 138 that is configured to receive a portion of a medical device through the lateral opening 138. For example, the first jaw 101, second jaw 102, and elastomeric insert 103 may include the lateral opening 138 that is configured to engage with a lateral port on a sheath to secure the lateral port to the clip and prevent the sheath from rotating.

As shown in FIGS. 1-3, the curved insert surfaces 164, 166 can be positioned closer to the proximal face 112 than the distal face 114 along the lateral face 132 of the first jaw 101 and the second jaw 102. In some aspects, the curved insert surfaces 164, 166 can be centered between the proximal face 112 and the distal face 114 along the lateral face 132. In some aspects, the curved insert surfaces 164, 166 can be positioned closer to the distal face 114 than the proximal face 112 along the lateral face 132.

In some aspects, each of the first insert 160 and the second insert 162 of the elastomeric insert 103 includes a distal portion 168. The distal portion 168 can be flat and extend distally through the distal portion 168 to a distal face of the elastomeric insert that is adjacent to the distal face 114. In some aspects, the distal portion 168 can have a distal depth that is less than the cavity depth d, as will be described in further detail in reference to FIGS. 4A-4D.

In some aspects, the elastomeric insert 103 is made from and/or includes elastomeric materials. The elastomeric insert 103 may be manufactured from various elastomeric materials and durometers, the various materials and durometers can change the coefficient of friction between the engaged devices (e.g., medical devices within medical clip 100) to provide increased or decreased grip on the device. In some aspects, lower durometer materials will have a higher static coefficient of friction. Examples of appropriate elastomeric materials include, but are not limited to: polyurethane in durometers of 20 A to 80 A (soft to firm), which can be cast, or injection molded; polyether urethane in durometers of 40 A-80 A, which can be injection molded; fluoroelastomers such as Viton™ in Durometers of 55 A-90 A, which can be injection molded; ethylene propylene diene monomer (EPDM) rubber in durometers from 50 A-70 A, which can be injection molded; silicone rubber in durometers of 20 A to 80 A, where silicone rubber can allow the medical clip 100 to be sterilized via autoclave due to the thermal properties of silicone rubber, which can be cast, or injection molded. Additional examples of materials for the elastomeric insert 103 include, but are not limited to: medical grade elastomeric materials, natural rubbers, styrene-butadiene block copolymers, polyisoprene, polybutadiene, ethylene propylene rubber, ethylene propylene diene rubber, silicone elastomers, fluoroelastomers, polyurethane elastomers, and nitrile rubbers. The elastomeric insert 103 may be coated with various materials (such as hydrophilic or hydrophobic materials) to provide higher or lower coefficient of friction.

In some aspects, the elastomeric insert 103 has a durometer from 20 A to 80 A, from 40 A to 80 A, from 55 A-90 A, from 50 A to 70 A, from 30 A to 70 A, from 40 A to 60 A, from 50 A to 60 A, from 20 A to 30 A, from 30 A to 40 A. While the elastomeric insert 103 can be manufactured from elastomeric materials, it is not limited to elastomeric materials.

FIGS. 4A-4D illustrate a variety of elastomeric inserts that are configured to accommodate a variety of Introduction Sheaths, Catheters, Guidewires, and Endoscope working channel ports shown in FIGS. 5A-5D and FIGS. 6-8. In some aspects, the elastomeric inserts 103, 203, 303, and 403 can share certain features with each other. The elastomeric inserts 103, 203, 303, and 403 can each be configured to be inserted into the medical clips described herein (e.g., medical clip 100). Like numbers refer to like components.

Figure 4A:
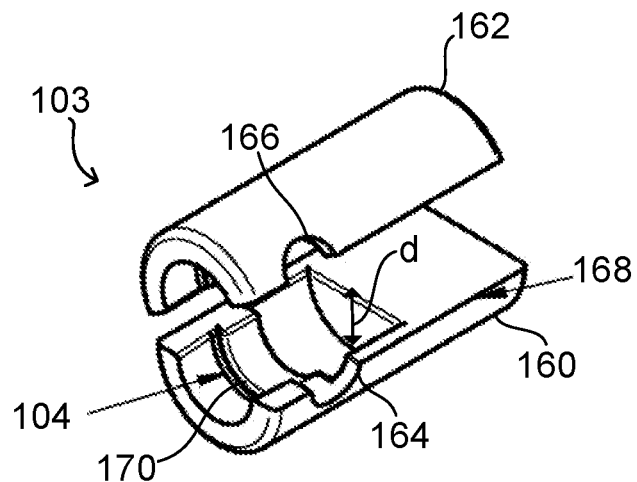
FIG. 4A shows a top, front perspective view of an example elastomeric insert that can be implemented in the medical clip.

FIG. 4A shows the elastomeric insert 103 removed from the medical clip 100, as described above. The elastomeric insert 103 includes the first insert 160 that is configured to be positioned in the first jaw 101 and the second insert 162 that is configured to be positioned in the second jaw 102. In some aspects, the first insert 160 and the second insert 162 can be symmetrical.

The elastomeric insert 103 defines the cavity 104 that can be in a proximal portion of the first insert 160 and the second insert 162, the proximal portion is closer to the proximal face 112 than the distal face 114. The cavity 104 has a cavity depth "d" in each of the first insert 160 and the second insert 162 that is dimensioned to receive a medical device between the first jaw 101 and the second jaw 102. The elastomeric insert 103 includes a curved insert surface 164 on the first insert 160 and a curved insert surface 166 on the second insert 162. The elastomeric insert 103 can include a ring 170 that extends circumferentially within each of the first insert 160 and the second insert 162. The ring 170 has a width that spans across the curved insert surface 164 and the curved insert surface 166. The ring 170 can have a thickness that reduces the cavity depth d across the width of the ring 170.

Figure 4B:
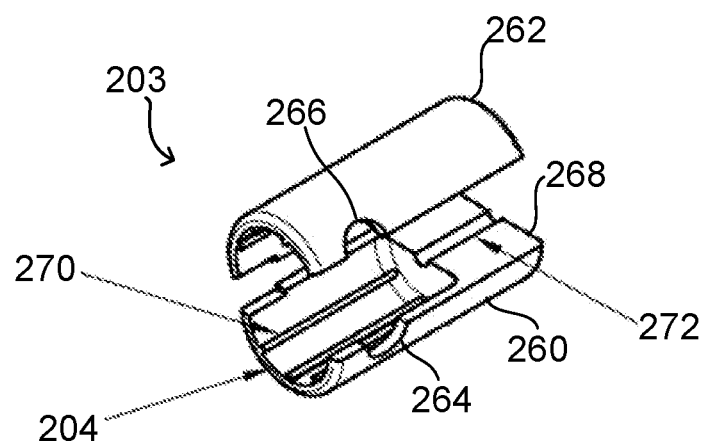
FIG. 4B shows a top, front perspective view of another elastomeric insert that can be implemented in the medical clip.

FIG. 4B shows an elastomeric insert 203 that is dimensioned to be positioned between the first jaw 101 and the second jaw 102. The elastomeric insert 203 includes a first insert 260 a second insert 262. In some aspects, the first insert 260 and the second insert 262 can be symmetrical. In some aspects, the first insert 260 is dimensioned to fill an internal profile of the first jaw 101 and the second insert 262 is dimensioned to fill an internal profile of the second jaw 102.

The elastomeric insert 203 defines the cavity 204 that can be in a proximal portion of the first insert 260 and the second insert 262. The cavity 204 can share features with the cavity 104 described above including a curved insert surface 264 on the first insert 260 and a curved insert surface 266 on the second insert 262. The cavity 204 can differ from the cavity 104 in some aspects. First, the cavity 204 can extend further distally than the cavity 104. Second, the cavity 204 can include one or more ribs 270 that extend distally through the cavity 204 at spaced out positions around a circumference of the cavity 204. In some aspects, the ribs 270 are flexible and/or collapsible to provide an increased grip on a portion of a medical device that is inserted in cavity 204. In some aspects, the ribs 270 are flexible and or collapsible to accommodate a variety of shapes found on the medical device that is inserted in cavity 204.

A distal portion 268 of the elastomeric insert 203 can differ from the distal portion 168 of the elastomeric insert 103. First, the distal portion 268 of elastomeric insert 203 can be shorter than distal portion 168 because the cavity 204 extends further distally than the cavity 104. Second, the distal portion 268 includes an auxiliary channel 272 that extends centrally through the distal portion 268. The auxiliary channel 272 can be configured to accommodate larger medical devices (e.g., catheters) within the medical clip.

Figure 4C:
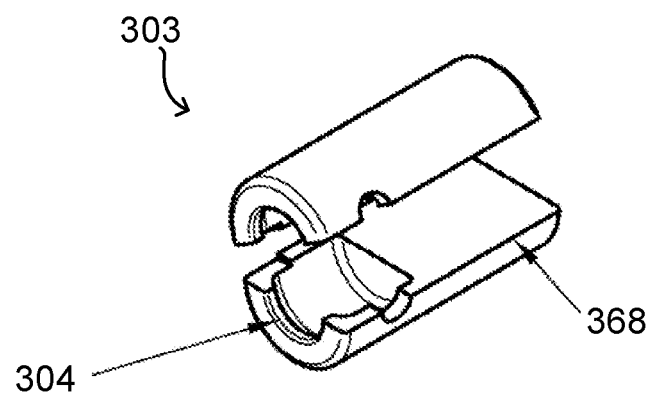
FIG. 4C shows a top, front perspective view of another elastomeric insert that can be implemented in the medical clip.
Figure 4D:
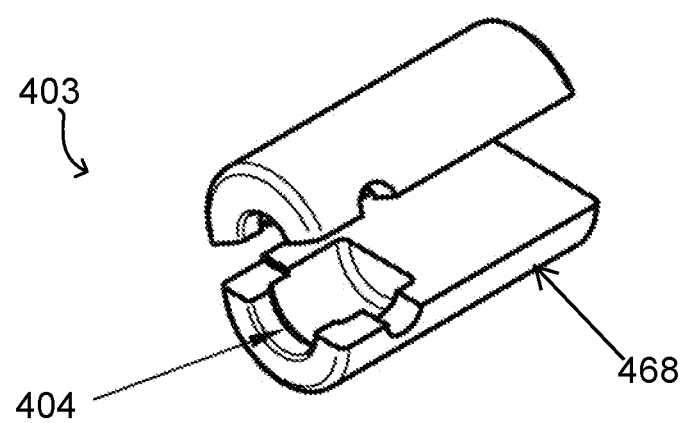
FIG. 4D shows a top, front perspective view of another elastomeric insert that can be implemented in the medical clip.
Figure 5A:
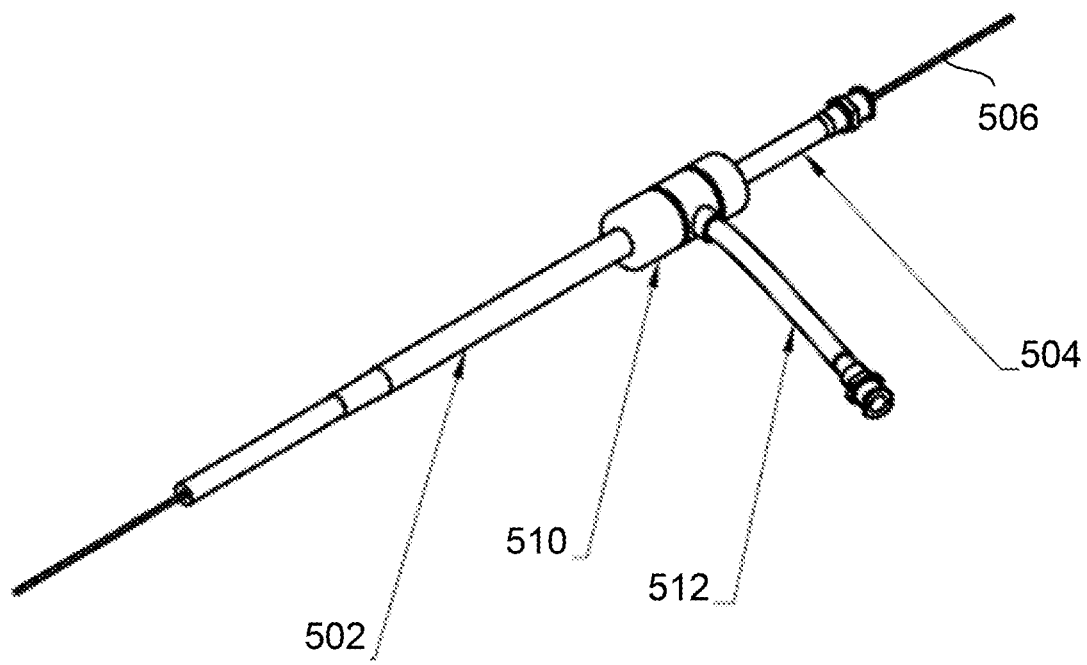
FIG. 5A shows a top, front perspective view of an example catheter assembly compatible with the elastomeric insert shown in FIG. 4A.
Figure 5B:
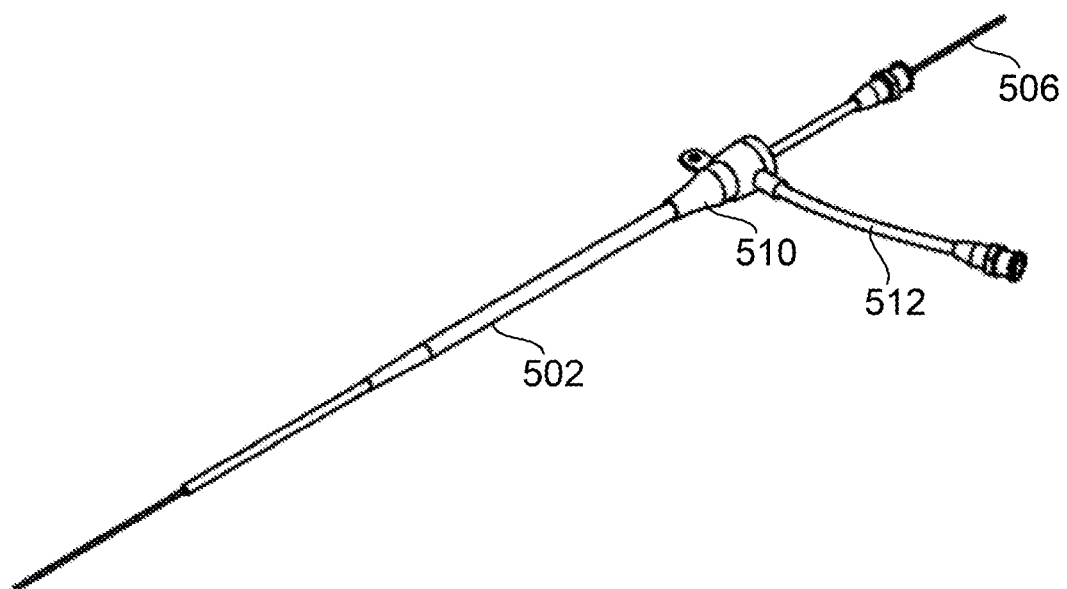
FIG. 5B shows a top, front perspective view of an example catheter assembly compatible with the elastomeric insert shown in FIG. 4B.
Figure 5C:
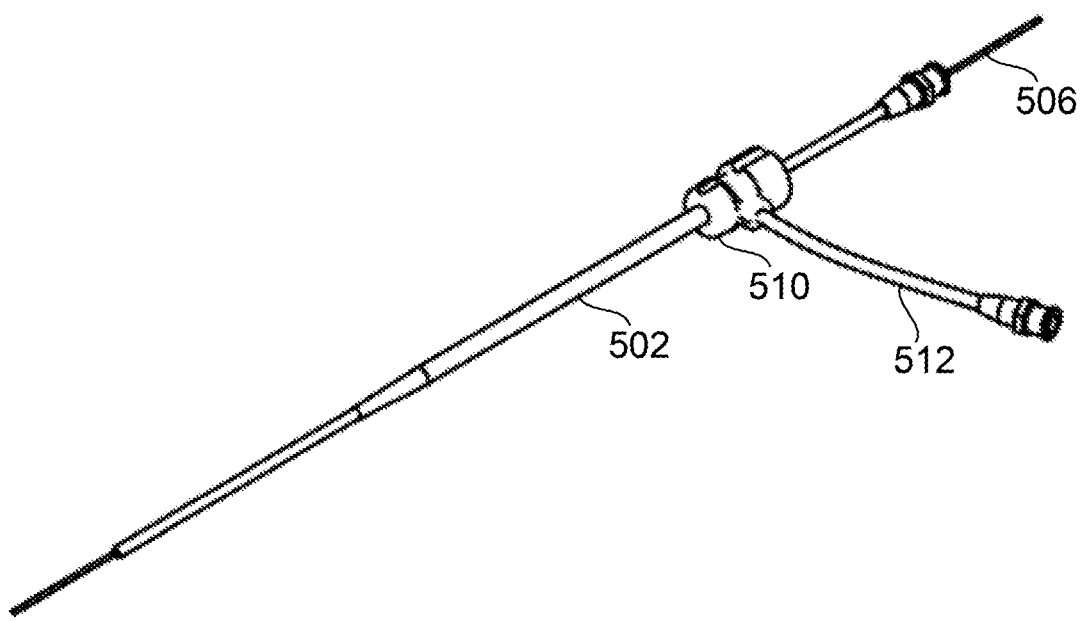
FIG. 5C shows a top, front perspective view of an example catheter assembly compatible with the elastomeric insert shown in FIG. 4C.
Figure 5D:
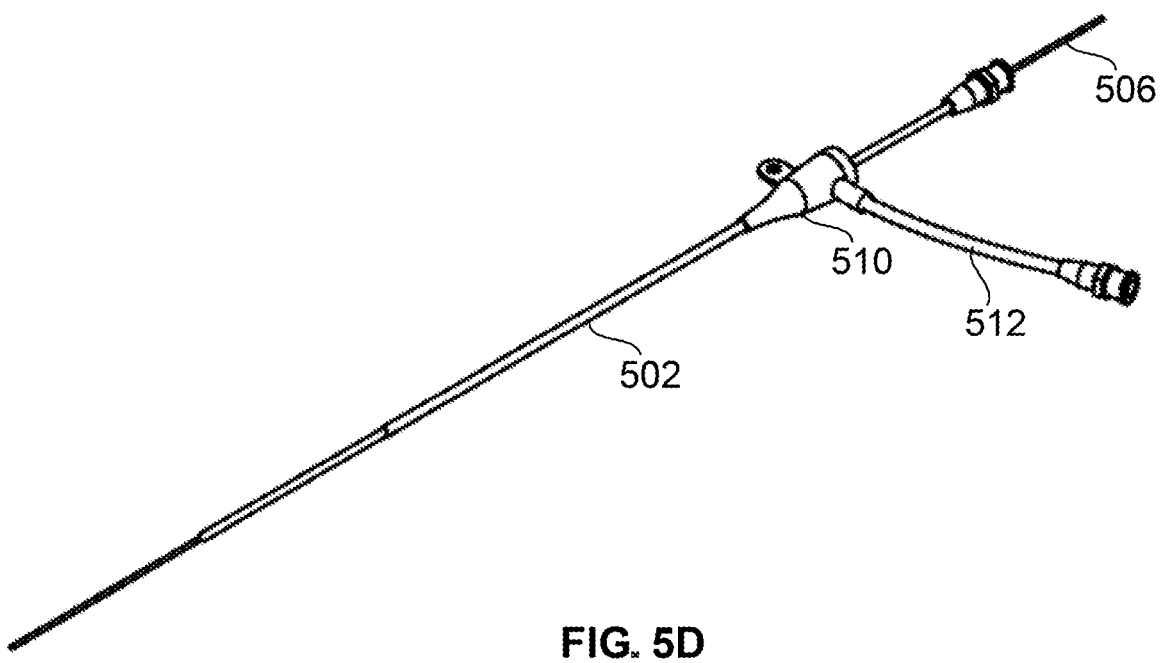
FIG. 5D shows a top, front perspective view of an example catheter assembly compatible with the elastomeric insert shown in FIG. 4D.

FIGS. 4C and 4D illustrate elastomeric inserts 303, 403 that provide varied lengths of a distal portion 368, 468. The varied lengths of distal portion 368, 468 provide different levels of friction to medical devices positioned within the medical clip.

FIGS. 5A-5B and FIGS. 6-8 illustrate various medical device configurations that the medical clip 100 and various elastomeric inserts 103, 203, 303, 403 are configured to retain and hold. The components may be configured in numerous ways providing optimal function in conjunction with introduction sheaths 502, catheters 504, guidewires 506, and endoscopes 508.

As illustrated in FIGS. 5A-5D, the introduction sheaths 502 can include a hub 510 that includes a lateral port 512 that extends from a lateral side of the sheath 502. The hubs 510 can take several shapes and sizes, and the medical clip described herein can receive the hub 510 within the elastomeric insert (e.g., elastomeric insert 103, 203, 303, 403) within the medical clip. The lateral port 512 can extend through a lateral opening (e.g., lateral opening 138) in the medical clip.

Figure 6:
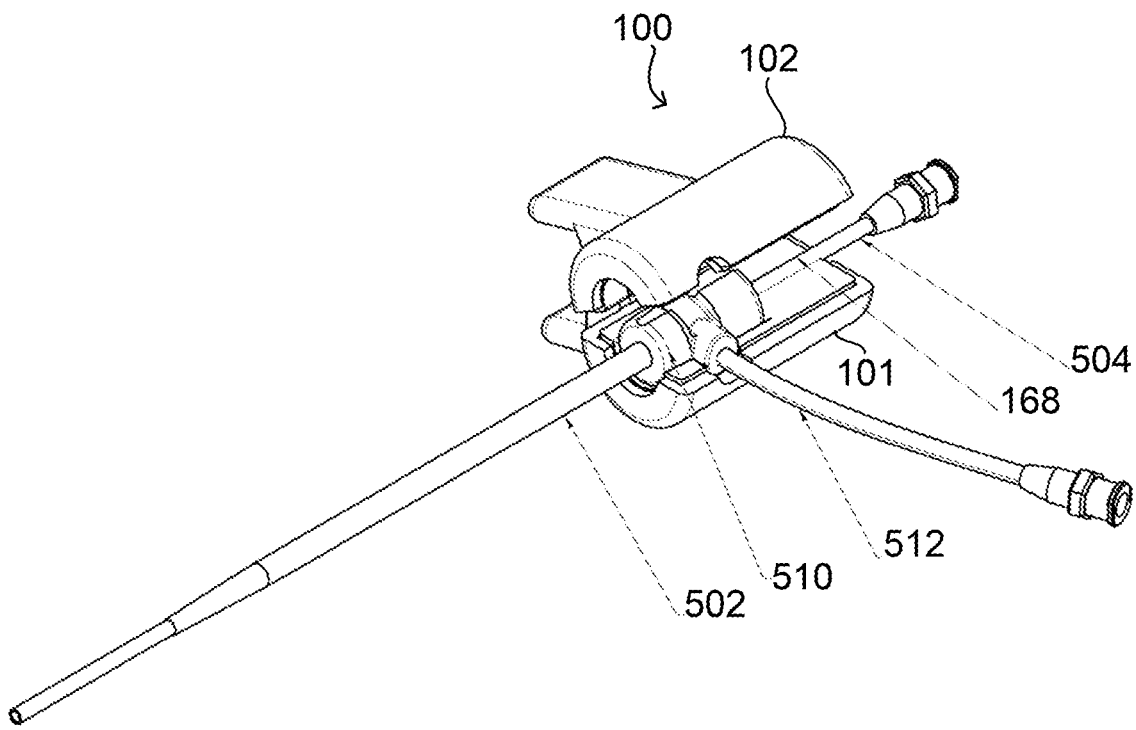
FIG. 6 shows a top, front perspective view of the medical clip in the open position with a catheter introducer and a catheter positioned in the medical clip.
Figure 7:
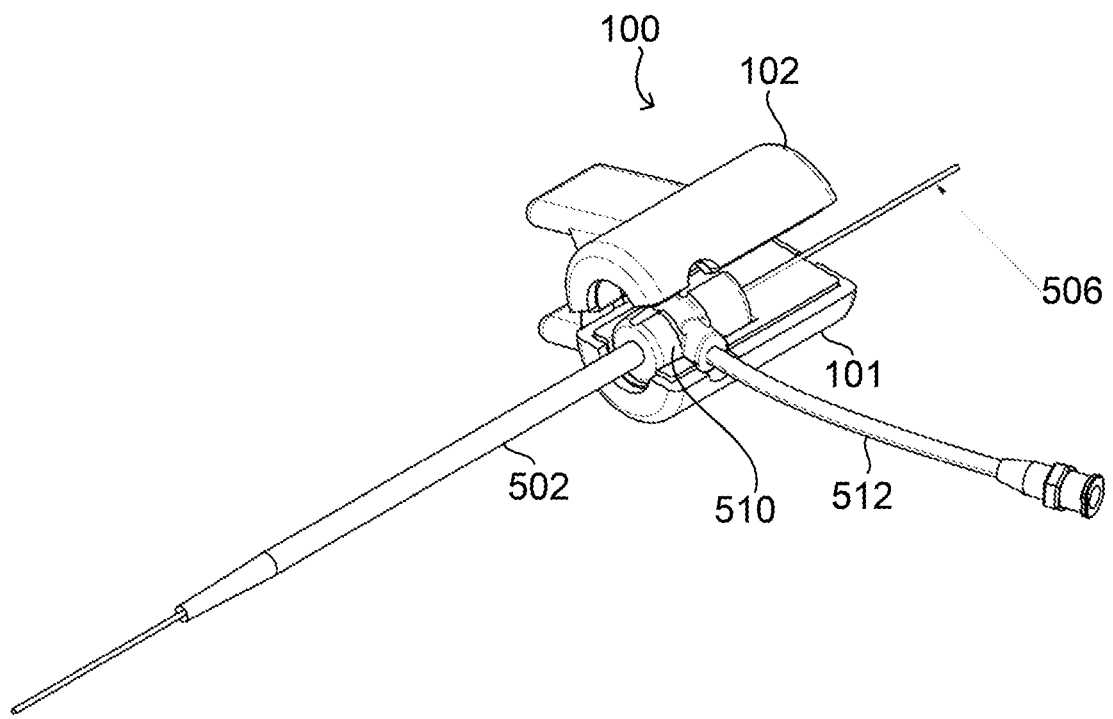
FIG. 7 shows a top, front perspective view of the medical clip in the open position with a catheter introducer and a guidewire positioned in the medical clip.

FIGS. 6 and 7 show the medical clip 100 with the hub 510 of a medical device received between the first jaw 101 and the second jaw 102.

Figure 8:
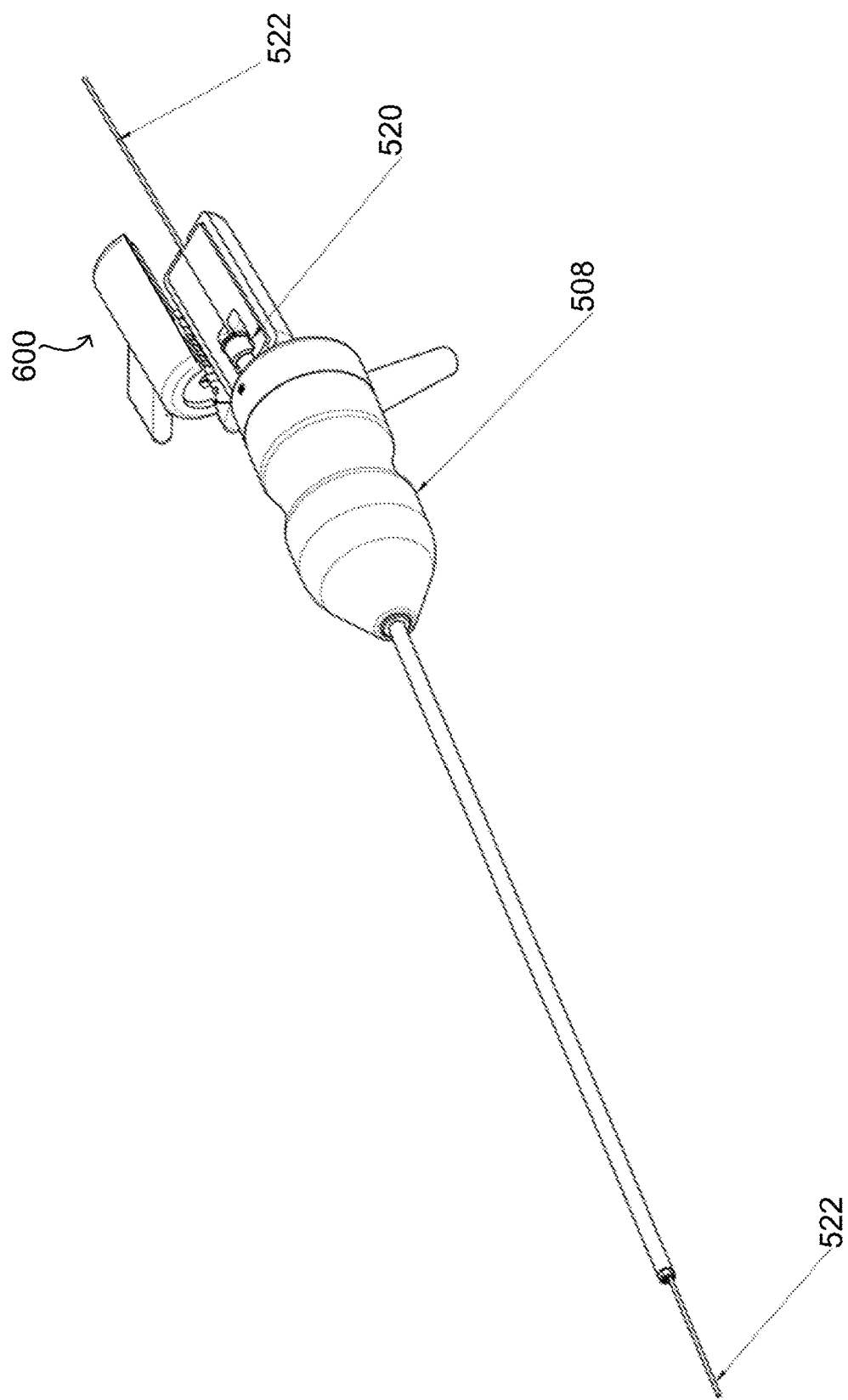
FIG. 8 shows a top, front perspective view of the medical clip in the open position with an endoscope positioned in the medical clip.

FIG. 8 shows an endoscope within a medical clip 600, the medical clip 600 sharing features with medical clip 100 and elastomeric inserts 103, 203, 303, and 403. The medical clip 600 can differ from medical clip 100 by omitting the lateral opening 138, if desired.

In FIGS. 6-8, the medical clip 100, 600 is configured to close and secure the elastomeric insert (e.g., elastomeric insert 103, 203, 303, 403) the hub 510 of a medical introduction sheath 502 or working channel inlet port 520 of an endoscope 508.

As illustrated herein, the medical clip 100 can be modified so that components are optimized for particular implementations. For example, various lengths of the first jaw 101 and the second jaw 102 and various lengths of elastomeric inserts 103, 203, 303, 403 can be implemented to change the engagement contact area with introduction sheaths 502, catheters 504, guidewires 506, and endoscopes 508. Various torsion springs 140 can be implemented to provide increased or decreased forces for closure of the medical clip 100. The medical clip 100 may be constructed of various plastics and elastomers to provide optimal cost benefits of a disposable device. The medical clip 100 components may be produced by various manufacturing processes including injection molding, elastomer casting, machining, and additive manufacturing processes. The medical clip 100 may be of various dimensions to accommodate introducer sheaths, catheters, guidewires, and endoscopes. The medical clip 100 may be constructed in a coaxial fashion, as depicted, or may have features placed off axis to direct the exit of the catheter, guidewire, or instrument optimally.

The medical clips described herein (e.g., medical clip 100, 600) can be implemented in medical procedures that incorporate the use of introduction sheaths 502, catheters 504, guidewires 506, and endoscopes 508. The medical clips 100, 600 can secure the catheter 504, guidewire 506, or instrument to the introduction sheath 502 or endoscope 508 and thus eliminate and/or reduce differential movement between the two.

As described above, the medical clip 100 includes a first jaw 101 and a second jaw 102 that are connected at the hinge 105 that has the torsion spring 140 that biases the first jaw 101 and second jaw 102 towards each other such that the medical clip is in the closed position shown in FIG. 3. The medical clip 100 can be closed to secure the elastomeric insert 103 to the hub 510 of the medical introduction sheath 502 or the working channel inlet port 520 of the endoscope 508. Adjacent to the hub 510 that is secured in the elastomeric insert 103 is a Clamping Region in the distal portion 168, 268, 368, 468 provided by the elastomeric insert 103 to secure a guidewire 506, catheter 504, or endoscopic Instrument 522 by friction as it exits from the sheath 502 or endoscope 508.

The medical clip 100 secures the catheters 504, guidewires 506, or instrument such that it will maintain position without damaging or misshaping either. When utilized to secure a catheter 504, the medical clip 100 fixes the catheter 504 in a targeted position and allows a single proceduralist to exchange guidewires (e.g., guidewire 506) and infuse through the catheter 504. This frees up a hand ordinarily used during the procedure to secure a catheter. This is particularly useful when catheters and guidewires have length exceeding an average arm span. In implementations that secure a guidewire 506 to the sheath 502, the medical clip 100 maintains wire position while exchanges are performed over the wire. In freeing the use of a hand, the medical clip 100 allows the single proceduralist to redirect their focus on another step and not lose the position of the guidewire 506 or catheter 504. In some implementations, a surgical assistant may not be needed to help maintain the relative positioning of instruments because the medical clip 100 achieves this function.

In operation, the medical clip 100 can be removed from sterile packaging. The medical clip 100 can be opened by the proceduralist (e.g., using a thumb and forefinger) and placed over the hub 510 or channel inlet port 520 and exiting catheter 504, guidewire 506 or endoscope 508. The cavity 104, 204, 304, 404 is provided within the elastomeric insert 103, 203, 303, 403 of the medical clip 100 to accept the hub 510 and/or channel inlet port 520. The medical clip 100 is closed by releasing the finger grips and allowing the torsion spring 140 to close the first jaw 101 and the second jaw 102. The exiting catheter 504, guidewire 506 or endoscope 508 is now fixed to the introduction sheath 502 or endoscope 508. The medical clip 100 may be removed and reinstalled any number of times to adjust position of the catheter 504, guidewire 506 or endoscope 508. At the conclusion of the procedure, the medical clip 100 can be discarded.

The medical clips 100, 600 described herein provide several advantages. These advantages include at least the following. First, the medical clip 100, 600 can remove the need for an assistant to maintain position of a catheter, guidewire or endoscopic instrument during a procedure. Second, the medical clip 100, 600 can facilitate the single handed use of the medical clip 100, 600 to secure catheter, guidewire, or instrument. Third, the medical clip 100, 600 can improve safety by removing securement of a catheter, guidewire, or instrument with an inappropriate device or adhesive to nearby sterile drapes or other equipment. Another advantage is the medical clip 100, 600 can improve safety by maintaining the catheter, guidewire or instrument integrity and by avoiding damage that can occur with current securing methods (e.g., securing to drapes or other equipment). The medical clip 100, 600 is advantageous by maintaining catheter, guidewire, or instrument position within the targeted anatomy. Another advantage is the medical clip 100, 600 allows for multiple sizes and types of catheters, guidewires, or instruments to be fixed with a single clip. Additionally, the medical clip 100, 600 improves safety and cleanliness of surgical materials by providing a sterilized medical clip that can be disposed of after one use.

While this specification contains many specific implementation details, these should not be construed as limitations on the scope of the disclosed technology or of what may be claimed, but rather as descriptions of features that may be specific to particular implementations of particular disclosed technologies. Certain features that are described in this specification in the context of separate implementations can also be implemented in combination in a single implementation in part or in whole. Conversely, various features that are described in the context of a single implementation can also be implemented in multiple implementations separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular implementations of the subject matter have been described. Other implementations are within the scope of the following claims.

What is claimed is:

1. A medical clip for holding a medical device, the medical clip comprising:
   a first jaw;
   a second jaw, the second jaw being rotatably coupled to the first jaw, the first jaw and the second jaw being rotatable with respect to each other between a closed position and an open position;
   an elastomeric insert configured to be positioned between the first jaw and the second jaw, the elastomeric insert defining a proximal cavity having a cavity depth that is dimensioned to receive the medical device between the first jaw and the second jaw, the proximal cavity having a length that is less than a length of the elastomeric insert;
   a first lever connected to the first jaw; and
   a second lever connected to the second jaw, the first lever and the second lever being configured to control each of the first jaw and the second jaw between the closed position and the open position;
   wherein, based on the medical clip being in the closed position, a distal face of each of the first jaw and the second jaw defines a distal opening configured to receive a portion of the medical device through the distal opening; and
   wherein, based on the medical clip being in the closed position, a proximal face of each of the first jaw and the second jaw define a proximal opening configured to receive a second portion of the medical device through the proximal opening;
   wherein a lateral face extends between the distal face and the proximal face of each of the first jaw and the second jaw, the lateral face of the first jaw defining a first part of a lateral opening and the lateral face of the second jaw defining a second part of the lateral opening, wherein the lateral opening is configured to accommodate a lateral port of the medical device.

2. The medical clip of claim 1, wherein the proximal cavity aligns with the proximal opening defined by the first jaw and the second jaw.

3. The medical clip of claim 1, wherein the elastomeric insert has a first insert connected to the first jaw and a second insert connected to the second jaw, the first insert and the second insert being symmetrical.

4. The medical clip of claim 1, wherein the elastomeric insert has a durometer from 20 A to 80 A.

5. The medical clip of claim 1, wherein the elastomeric insert comprises collapsible ribs that extend circumferentially around the proximal cavity, the collapsible ribs being configured to collapse when the medical device is inserted within the proximal cavity.

6. The medical clip of claim 1, wherein a distal portion of the elastomeric insert defines an auxiliary channel that extends distally through the distal portion to a distal face of the elastomeric insert.

7. The medical clip of claim 1, wherein a distal portion of the elastomeric insert is flat and extends distally through the distal portion to a distal face of the elastomeric insert.

8. The medical clip of claim 1, wherein the first jaw and the second jaw are symmetrical.

9. The medical clip of claim 1, further comprising:
a hinge connected to each of the first jaw and the second jaw, the first jaw and the second jaw being rotatable about the hinge.

10. The medical clip of claim 9, further comprising;
a torsion spring disposed about the hinge providing force to close the first and second jaws automatically when the first and second levers are released.

11. The medical clip of claim 1, wherein the elastomeric insert further comprises a distal portion that has a distal depth that is less than the cavity depth.

12. The medical clip of claim 1, wherein each of the first jaw and the second jaw has a curved shape that extends between the proximal face and the distal face.

13. A clip for securing a medical device, the clip comprising:
a first jaw having a curved shape that extends between a proximal face of the clip to a distal face of the clip;
a second jaw having a curved shape that extends between the proximal face of the clip and the distal face of the clip, the first jaw and the second jaw being rotatable with respect to each other between a closed position and an open position;
an elastomeric insert having a first insert configured to be received within the first jaw and a second insert configured to be received within the second jaw, the elastomeric insert defining a proximal cavity having a cavity depth that is dimensioned to receive the medical device between the first jaw and the second jaw, the proximal cavity having a length that is less than a length of the elastomeric insert;
a first lever connected to the first jaw; and
a second lever connected to the second jaw, the first lever and the second lever being configured to control each of the first jaw and the second jaw between the closed position and the open position;
wherein, based on the clip being in the closed position, a distal face of each the first jaw and the second jaw defines a distal opening configured to receive a portion of the medical device through the distal opening; and
wherein, based on the clip being in the closed position, a proximal face of each of the first jaw and the second jaw define a proximal opening configured to receive a second portion of the medical device through the proximal opening;
wherein a lateral face extends between the distal face and the proximal face of each of the first jaw and the second jaw, the lateral face of the first jaw defining a first part of a lateral opening and the lateral face of the second jaw defining a second part of the lateral opening, wherein the lateral opening is configured to accommodate a lateral port of the medical device.

14. The clip of claim 13, wherein the proximal cavity aligns with the proximal opening defined by the first jaw and the second jaw.

15. The clip of claim 13, wherein the first insert and the second insert are symmetrical.

16. The clip of claim 13, wherein the elastomeric insert has a durometer from 20 A to 80 A.

17. The clip of claim 13, wherein a distal portion of the elastomeric insert is flat and extends distally through the distal portion to a distal face of the elastomeric insert.

18. The clip of claim 13, wherein the first jaw and the second jaw are symmetrical.

19. A method of holding a medical device using a clip, the method comprising:
providing the clip for holding the medical device, the clip comprising:
a first jaw,
a second jaw, the second jaw being rotatably coupled to the first jaw, the first jaw and the second jaw being rotatable with respect to each other about a hinge between a closed position and an open position,
an elastomeric insert positioned between an internal surface of the first jaw and an internal surface of the second jaw, the elastomeric insert having a proximal cavity with a cavity depth that is dimensioned to receive the medical device between the first jaw and the second jaw, the proximal cavity having a length that is less than a length of the elastomeric insert;
a first lever connected to the first jaw, and
a second lever connected to the second jaw, the first lever and the second lever being configured to control each of the first jaw and the second jaw between the closed position and the open position;
wherein a lateral face extends between a distal face and a proximal face of each of the first jaw and the second jaw, the lateral face of the first jaw defining a first part of a lateral opening and the lateral face of the second jaw defining a second part of the lateral opening, wherein the lateral opening is configured to accommodate a lateral port of the medical device;
opening the first and second jaws to place the clip in the open position;
inserting a portion of the medical device in the proximal cavity of the elastomeric insert; and
closing the first and second jaws to place the clip in the closed position such that the medical device is held by the elastomeric insert.

\* \* \* \* \*